United States Patent [19]

Langenscheid, deceased et al.

[11] 4,122,172

[45] Oct. 24, 1978

[54] β-D-1-(6-AMINO-9H-PURIN-9-YL)-1-DEOXY-2,3-DI-O-NITRORIBOFURANURONE-THYLAMIDE

[75] Inventors: Erhard Langenscheid, deceased, late of Karlsruhe, Fed. Rep. of Germany, by Ursula Sickelmann, guardian of sole heir Markus Langenscheid; Kurt Klemm, Allensbach, Fed. Rep. of Germany

[73] Assignee: Byk Gulden Lomberg Chemische Fabrik GmbH, Fed. Rep. of Germany

[21] Appl. No.: 851,381

[22] Filed: Nov. 14, 1977

Related U.S. Application Data

[62] Division of Ser. No. 666,311, Mar. 12, 1976, abandoned.

[30] Foreign Application Priority Data

Mar. 18, 1975 [LU]  Luxembourg ............................ 72078

[51] Int. Cl.² ........................ A61K 31/70; C07H 19/06

[52] U.S. Cl. ............................................. 424/180; 536/26
[58] Field of Search ............................................. 536/26

[56] References Cited

U.S. PATENT DOCUMENTS

| | | | |
|---|---|---|---|
| 3,830,795 | 8/1974 | Prasad et al. | 536/26 |
| 3,830,796 | 8/1974 | Prasad et al. | 536/26 |
| 3,832,341 | 8/1974 | Duschinsky | 536/26 |
| 3,903,073 | 9/1975 | Prasad et al. | 536/26 |
| 3,914,414 | 10/1975 | Stein et al. | 536/26 |
| 3,914,415 | 10/1975 | Stein et al. | 536/26 |

*Primary Examiner*—Johnnie R. Brown
*Assistant Examiner*—Blondel Hazel
*Attorney, Agent, or Firm*—Berman, Aisenberg & Platt

[57] ABSTRACT

The title compound, prepared by nitrating β-D-1-(6-amino-9H-purin-9-yl)-1-deoxyribofuranuronethyla-mide, is physiologically active and pharmacologically acceptable. It is useful for increasing coronary blood flow and is administrable, e.g., in the form of a medicament composition.

6 Claims, No Drawings

β-D-1-(6-AMINO-9H-PURIN-9-YL)-1-DEOXY-2,3-DI-O-NITRORIBOFURANURONETHYLAMIDE

RELATED APPLICATION

This application is a division of application Ser. No. 666,311, filed Mar. 12th, 1976 and now abandoned.

BACKGROUND

β-D-1-(6-amino-9H-purin-9-yl)-1-deoxyribofuranuronic acid esters (German Offenlegungsschrift No. 2,244,215), β-D-1-(6-amino-9H-purin-9-yl)-1-deoxyribofuranuronamides (German Offenlegungsschrift No. 2,034,785) and β-D-1-(6-amino-9H-purin-9-yl)-1-deoxyribofuranose derivatives nitrated on the ribose radical (German Offenlegungsschrift No. 2,105,560) have an advantageous cardiac action.

SUMMARY OF THE INVENTION

β-D-1-(6-amino-9H-purin-9-yl)-1-deoxy-2,3-di-O-nitroribofuanuronethylamide is prepared, e.g., by reacting the nucleoside, β-D-1-(6-amino-9H-purin-9-yl)-1-deoxyribofuranonethylamide, with a reagent transferring $-NO_2$ groups. This reaction with a reagent transferring $-NO_2$ groups is carried out in a conventional manner. For example, nitric acid or, preferably, a mixture of nitric acid and acetic anhydride are used for this purpose.

DETAILS

The title compound is conveniently prepared from the noted nucleoside and a mixture of nitric acid and acetic anhydride; reaction is effected at a low temperature, preferably between $-70°$ C. and room temperature ($20°$ C.). Generally, the purine nucleoside is simply stirred into cooled fuming nitric acid and the resulting mixture is left at a low temperature until the reaction is terminated. Under these relatively mild conditions the glycoside bond, which is sensitive to acidic hydrolysis, is substantially protected against attack. In order to protect the amino group of the adenosine radical, a nitrite catcher, for example urea, is advantageously added to the nitric acid to protect the adenosine radical against deamination by nitrous acid. The reaction, which rapidly progresses to the formation of 2'- and, respectively, 3'-mononitrate esters and 2',3'-dinitrate esters, is terminated within a few hours when maintained within the indicated temperature range.

For further processing, the reaction mixture is poured onto ice and neutralized with solid sodium hydrogen carbonate. The mixture of nitrate esters is removed from the aqueous phase by extraction, for example, with ethyl acetate and then separated by fractional crystallization and/or column chromatography.

The compound of this invention is characterized by a very satisfactory action on the heart and on blood circulation and, more especially, it has a surprisingly-pronounced coronary-dilating action. The unusually-long duration (persistence) of its action is particularly surprising. That this action is also achieved on oral administration is of special significance. This compound is useful in the treatment of and for relieving the pain and other symptoms associated with angina pectoris.

Preliminary investigations revealed that, from highly effective (with respect to their action on the heart) prior-art adenosine derivatives, compound A (see Table I) exerts an exceptionally-strong and long-lasting action. The compound of this invention was therefore compared with compound A.

The results shown in Table I were obtained by using the well-known method of Langendorff in a modified version from isolated hearts of guinea-pigs.

TABLE 1

ACTION ON CORONARY FLOW

|   | $R^1$ | $R^2$ | Efficacy* [%] | Duration of Effect** [min] | [%] |
|---|---|---|---|---|---|
| A | OH | OH | 100 | 15 | 100 |
| B | $ONO_2$ | $ONO_2$ | 118 | 38 | 253 |

*relative area below the graph of the coronary flow versus time.
**time from maximum value of coronary flow to point where original value is reached again.

The range of concentration was from 0.001 to 5.0 μg of active compound per ml of nutritive solution (Krebs-Henseleit). The average effective concentration ($CE_{50}$) from which the results of Table I were obtained ranged from 0.005 to 1.0 μg/ml.

As one measure for the long-lasting action the relative area below the graph of the coronary flow versus time was determined. This integration was carried out starting at the time at which the nutritive solution (containing the active substance) was replaced by a neutral nutritive solution (i.e. when coronary flow reached a maximum value) and continuing until coronary flow fell back to its original level. These results are reproduced in column 2 of Table I.

As a further parameter indicating long-lasting action, the time of fading away of the effectiveness was determined; that is the time from the point at which coronary flow reached its maximum value to the point the coronary flow was reduced again to its original level. These results are reproduced in column 3 of Table I.

Table I shows that new compound B reflects a very strong action with regard to coronary flow and that this action persists for a longer period of time than that of prior-art compound A.

Medicaments which comprise the compound of this invention as an active ingredient optionally comprise other pharmacologically-active substances, for example, cardiac glycosides, beta-receptor blockers, sedatives, tranquillizers and substances which reduce the cholesterine and the lipid level. The medicaments are produced in a conventional manner, for example, for enteral, percutaneous or parenteral administration by combining the active substance with a suitable pharmaceutical vehicle, for example, filler, a diluent, a corrective material and/or other components which are conventional for medicaments. The medicaments are produced, for example, in a solid form as tablets or capsules or in a liquid form as solutions or suspensions. If required, they are stabilized and/or comprise adjuvants, such as preserving, stabilizing, moistening or emulsifying materials, salts for changing osmotic pressure or buffers. Preparations suitable for oral administration optionally comprise flavoring and sweetening materials. The pharmaceutical vehicles optionally also comprise conventional diluting or tableting additives, such as cellulose powder, maize starch, lactose, and talcum, as are conventional for such purposes.

The production of the pharmaceutical preparations is carried out conventionally, for example, by means of conventional mixing, granulating or dragee-making methods. The pharmaceutical preparations comprise, e.g., approximately 0.1% to approximately 50%, preferably approximately 1% to approximately 10%, by weight of the active compound in accordance with the invention. The administration is enteral, for example oral, or parenteral, the individual doses lying between 0.05 and 50 mg, preferably between 0.1 and 5 mg, of the active compound. The indicated doses are administered from 1 to 4 times daily, for example at mealtimes and/or in the evening, to adult patients in need of increased coronary blood flow.

The individual dose, the frequency of administration and the duration of treatment are in accordance with the nature and severity of the condition being treated.

The invention, therefore, includes medicaments, which are characterized by a content of the compound of the invention, optionally in combination with other pharmacologically-active material, and the production of such medicaments.

| Example of a Batch for the Production of 100,000 Tablets (each containing 1 mg of active substance) |
| --- |
| 0.1 kg β-D-1-(6-amino-9H-purin-9-yl)-1-deoxy-2,3-di-D-nitroribofuranuronethylamide (1) |
| 8.2 kg maize starch (2) |
| 7.2 kg lactose (3) |
| 0.3 kg amorphous silicic acid (4) |
| 0.4 kg sodium lauryl sulfate (5) |
| 0.5 kg gelatine (6) |
| 0.1 kg glycerine (7) |
| 0.5 kg talcum (8) |
| 0.2 kg magnesium stearate (9) |
| 17.5 kg |

The active substance (1) is mixed with 1 kg of (3) and the mixture is finely powdered. To this mixture 7.20 kg of (2) and the rest of (3), (4) and (5) are added. After mixing and sieving, this powder mixture is moistened with a solution of (6) and (7) in 7 liters of water and granulated through a sieve with a mesh width of 1.25 mm. This granulate is dried and thoroughly mixed with the rest of (2), (8) and (9) and then pressed on a rotaring machine to form tablets with a weight of 175 mg.

| Example of a Batch for the Production of 100,000 Capsules (each containing 1 mg of active substance) |
| --- |
| 0.10 kg β-D-1-(6-amino-9H-purin-9-yl)-1-deoxy-2,3-di-O-nitroribofuranuronethylamide (1) |
| 6.20 kg lactose (2) |
| 2.25 kg carboxymethylcellulose (3) |
| 0.45 kg polyvinylpyrrolidone (4) |
| 9.00 kg |

(1), (2) and (3) are mixed and finely powdered. (4) is dissolved in 3 liters of water. The powder mixture is moistened with the resulting solution and granulated through a sieve with a mesh width of 1.25 mm. The granulate is dried and capsules of size 4 are filled with 90 mg of the dried granulate.

EXAMPLE 1

700 mg of urea are added (while stirring) to 11.0 ml of ice-cooled 100% $HNO_3$, and then 2.0 g (6.5 mmoles) of β-D-1-(6-amino-9H-purin-9-yl)-1-deoxyribofuranuronethylamide are added thereto in small portions within a period of approximately 20 minutes. The resulting solution is stirred for 3 hours on an ice bath and then poured onto 50 ml of ice/water and neutralized with solid $NaHCO_3$. Following this, the preparation is extracted with five 20-ml portions of ethyl acetate. The organic phases are dried over $Na_2SO_4$ and condensed in vacuo. 2.3 g of yellow syrup are thus produced. In a thin layer chromatogram [silica gel, $CHCl_3/CH_3CN$/MeOH (5 to 4 to 1)] two closely adjacent spots are found.

β-D-1-(6-amino-9H-purin-9-yl)-1-deoxy-2,3-di-O-nitroribofuranuronethylamide has an Rf value of 0.7 and β-D-1-(6-amino-9H-purin-9-yl)-1-deoxy-3-O-nitroribofuranuronethylamide has an Rf value of 0.5.

The 2.3 g of syrup are taken up in 20 ml of $CHCl_3/CH_3CN$ (6 to 4). The undissolved residue is filtered off and, after recrystallization from 50 ml of methanol, yields 250 mg (11%) of β-D-1-(6-amino-9H-purin-9-yl)-1-deoxy-3-O-nitroribofuranuronethylamide in the form of colorless needles.

The filtrate is taken up on a silica gel column (3.2 cm in diameter × 70 cm). Elution is first carried out with 500 ml of $CHCl_3/CH_3CN$ (6 to 4), then with successive 100-ml portions of $CHCl_3/CH_3Cn$ (6 to 4), to which increasing quantities (2, 4, 6 and 8%, respectively) of MeOH are added and finally with 1 liter of $CHCl_3/CH_3CN$/MeOH (5 to 4 to 1). Fractions of approximately 20 ml are taken and their composition is checked chromatographically on silica gel foils in $CHCl_3/CH_3CN$/MeOH (5 to 4 to 1). The corresponding fractions are condensed, yielding 400 mg (15.5%) of β-D-1-(6-amino-9H-purin-9-yl)-1-deoxy-2,3-di-O-nitroribofuranuronethylamide and 700 mg (30%) of β-D-1-(6-amino-9H-purin-9-yl)-1-deoxy-3-O-nitroribofuranuronethylamide, each as a colorless foam.

β-D-1-(6-amino-9H-purin-9-yl)-1-deoxy-2,3-di-O-nitroribofuranuronethylamide is recrystallized from $CH_3CN$ to provide colorless needles with a fusing point of 163° to 165° C., with decomposition.

β-D-1-(6-amino-9H-purin-9-yl)-1-deoxy-3-O-nitroribofuranuronethylamide is produced as colorless needles (on recrystallization from methanol) with a fusing point of 200° C., with decomposition.

The β-D-1-(6-amino-9H-purin-9-yl)-1-deoxyribofuranuronethylamide used as a starting material is produced, e.g., by the method described in German Offenlegungsschrift No. 2,034,785.

The preceding text discloses to the artisan what the invention is, how it is prepared and how it is used. Indicated and illustrated compositions are subject to numerous variations, which are readily apparent to those skilled in the art.

What is claimed is:

1. The compound which is β-D-1-(6-amino-9H-purin-9-yl)-1-deoxy-2,3-di-O-nitroribofuranuronethylamide.

2. A pharmaceutical composition comprising active ingredient and a suitable pharmaceutical vehicle, the active ingredient comprising from 0.1 to 50 percent by weight, based on the total composition weight, of the compound according to claim 1.

3. A pharmaceutical composition according to claim 2 wherein said compound is in admixture with another pharmaceutically- and chemically-compatible pharmacologically-active substance.

4. A pharmaceutical composition according to claim 2 in unit dosage form, each unit dosage having from 0.05 to 50 milligrams of said compound.

5. A process which comprises administering to a mammal, enterally or parenterally, an amount of the compound of claim 1 sufficient to induce coronary dilation or to increase coronary blood flow.

6. A process which comprises administering to a patient, enterally or parenterally, in need of coronary dilation or increased coronary blood flow an effective amount of a pharmaceutical composition according to claim 2.

* * * * *